(12) United States Patent
Jiang et al.

(10) Patent No.: US 10,316,356 B1
(45) Date of Patent: Jun. 11, 2019

(54) METHOD OF CONSTRUCTING SEQUENCING LIBRARY WITH BUBBLE-SHAPED ADAPTOR ELEMENT

(71) Applicant: MGI Tech Co., Ltd., Shenzhen (CN)

(72) Inventors: Yuan Jiang, Shenzhen (CN); Kai Tian, Shenzhen (CN); Xia Zhao, Shenzhen (CN); Wenwei Zhang, Shenzhen (CN); Huaiqian Xu, Shenzhen (CN); Hui Jiang, Shenzhen (CN); Radoje Drmanac, Los Altos Hills, CA (US); Chunyu Geng, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 182 days.

(21) Appl. No.: 15/528,353

(22) PCT Filed: Nov. 21, 2014

(86) PCT No.: PCT/CN2014/091953
§ 371 (c)(1),
(2) Date: May 19, 2017

(87) PCT Pub. No.: WO2016/078096
PCT Pub. Date: May 26, 2015

(51) Int. Cl.
*C12Q 1/6806* (2018.01)
*C12Q 1/6855* (2018.01)
*C12Q 1/6869* (2018.01)

(52) U.S. Cl.
CPC ......... *C12Q 1/6855* (2013.01); *C12Q 1/6806* (2013.01); *C12N 2310/53* (2013.01); *C12N 2310/532* (2013.01); *C12Q 1/6869* (2013.01); *C12Q 2535/122* (2013.01)

(58) Field of Classification Search
CPC .. C12Q 1/6855; C12Q 1/6869; C12Q 1/6806; C12Q 2535/122; C12N 2310/53; C12N 2310/532
See application file for complete search history.

(56) References Cited

U.S. PATENT DOCUMENTS

| | | | |
|---|---|---|---|
| 2009/0176652 A1 | 7/2009 | Dahl et al. | |
| 2010/0167954 A1 | 7/2010 | Earnshaw et al. | |

FOREIGN PATENT DOCUMENTS

| | | | |
|---|---|---|---|
| CN | 102296065 A | 12/2011 | |
| CN | 102628079 A | 8/2012 | |
| WO | 2008023179 A2 | 2/2008 | |
| WO | 2009032167 A1 | 3/2009 | |

OTHER PUBLICATIONS

International Search Report issued for PCT/CN2014/091953 dated Sep. 8, 2015.
Written Opinion of the International Searching Authority issued for PCT/CN2014/091953 dated Sep. 8, 2015.

*Primary Examiner* — Jeremy C Flinders
(74) *Attorney, Agent, or Firm* — Westman, Champlin & Koehler, P.A.; Z. Peter Sawicki (57) ABSTRACT

Provided is a method of constructing a sequencing library using an adaptor element in a bubble shape. The bubble-shaped adaptor is ligated to a DNA fragment respectively at the 3'-terminal and the 5'-terminal i.e., two bubble-shaped adaptors with same sequences are ligated in one step. The bubble-shaped adaptor-ligated product is then amplified with a primer complementary to the 3'-terminal of the long-chain nucleic acid of the bubble-shaped adaptor, so as to replace the non-paired sequence in the short-chain nucleic acid.

20 Claims, 3 Drawing Sheets
Specification includes a Sequence Listing.

SEQUENCE LISTING

```
<160> NUMBER OF SEQ ID NOS: 9

<210> SEQ ID NO 1
<211> LENGTH: 57
<212> TYPE: DNA
<213> ORGANISM: Artificial sequence
<220> FEATURE:
<221> NAME/KEY: Modified base
<222> LOCATION: (1)..(1)
<223> OTHER INFORMATION: Phosphorylation modification
<220> FEATURE:
<223> OTHER INFORMATION: Long-chain nucleic acid of adaptor element 1

<400> SEQUENCE: 1
actgctgagt cgagatgtca taaatctgac aaggtcgcca gccctgagtg cttcgaa       57

<210> SEQ ID NO 2
<211> LENGTH: 41
<212> TYPE: DNA
<213> ORGANISM: Artificial sequence
<220> FEATURE:
<223> OTHER INFORMATION: Short-chain nucleic acid of adaptor element 1
```

```
<400> SEQUENCE: 2
cgaagcactc aaggtcgcca gccctcagta cgtcagcagt t                41

<210> SEQ ID NO 3
<211> LENGTH: 39
<212> TYPE: DNA
<213> ORGANISM: Artificial sequence
<220> FEATURE:
<221> NAME/KEY: Modified base
<222> LOCATION: (1)..(1)
<223> OTHER INFORMATION: Phosphorylation modification
<220> FEATURE:
<223> OTHER INFORMATION: Long-chain nucleic acid of adaptor element 2

<400> SEQUENCE: 3
agtcggaggc caagcgtgct taggatgagt gctctcgaa                   39

<210> SEQ ID NO 4
<211> LENGTH: 33
<212> TYPE: DNA
<213> ORGANISM: Artificial sequence
<220> FEATURE:
<223> OTHER INFORMATION: Short-chain nucleic acid of adaptor element 2

<400> SEQUENCE: 4
cgagagcact ccatgtagtg tacgatccga ctt                         33

<210> SEQ ID NO 5
<211> LENGTH: 20
<212> TYPE: DNA
<213> ORGANISM: Artificial sequence
<220> FEATURE:
<223> OTHER INFORMATION: Forward primer of adaptor element 1

<400> SEQUENCE: 5
aggucgccag cccucagtac                                        20

<210> SEQ ID NO 6
<211> LENGTH: 20
<212> TYPE: DNA
<213> ORGANISM: Artificial sequence
<220> FEATURE:
<223> OTHER INFORMATION: Reverse primer of adaptor element 1

<400> SEQUENCE: 6
agggcuggcg accutgtcag                                        20

<210> SEQ ID NO 7
<211> LENGTH: 19
<212> TYPE: DNA
<213> ORGANISM: Artificial sequence
<220> FEATURE:
<223> OTHER INFORMATION: Forward primer of adaptor element 2

<400> SEQUENCE: 7
tcctaagcac gcttggcct                                         19

<210> SEQ ID NO 8
<211> LENGTH: 22
<212> TYPE: DNA
<213> ORGANISM: Artificial sequence
<220> FEATURE:
<223> OTHER INFORMATION: Reverse primer of adaptor element 2

<400> SEQUENCE: 8
catgtagtgt acgatccgac tt                                     22
```

```
<210> SEQ ID NO 9
<211> LENGTH: 24
<212> TYPE: DNA
<213> ORGANISM: Artificial sequence
<220> FEATURE:
<223> OTHER INFORMATION: Bridge fragment for adaptor element 2

<400> SEQUENCE: 9
gtacactaca tgtcctaagc acgc                                            24
```

METHOD OF CONSTRUCTING SEQUENCING LIBRARY WITH BUBBLE-SHAPED ADAPTOR ELEMENT

CROSS-REFERENCE TO RELATED APPLICATION

This application is the U.S. national phase of PCT Application No. PCT/CN2014/091953 filed with the State Intellectual Property Office of P. R. China on Nov. 21, 2014, the entire content of which is incorporated herein by reference.

FIELD

The present disclosure relates to the field of biotechnology, in particular, to a method of constructing a sequencing library using an adaptor element in a bubble shape, a constructed sequencing library, and a use thereof.

BACKGROUND

As being capable of detecting all nucleotide sequences of a species to a whole genome, the whole genome sequencing technology may obtain all genetic information of a whole genome in an individual with accuracy as high as 99.99%. With the development of the next generation high-throughput sequencing technology, it has become more and more rapid to sequence with high accuracy and low cost, therefore the whole genome sequencing technology has been widely used in research.

The Complete Genomics (CG) sequencing, which is a cyclic single stranded DNA based sequencing, should be carried out in the presence of known sequenced adaptors. In general, a conventional process for constructing a whole genome library based on CG sequencing platform is achieved with two sets of adaptors, each set of which includes two different sequences. Such a process involves cumbersome steps and thus is time-consumed.

The present disclosure is proposed to reduce steps of ligating adaptors in the library construction based on CG sequencing platform, and thus shortening overall time consumed for the library construction.

SUMMARY

In view of the above deficiencies of the related art, it is objects of the present disclosure to provide a method of constructing a sequencing library using an adaptor in a bubble shape, a constructed sequencing library and a use thereof. In embodiments of the present disclosure, library construction is optimized with a bubble-shaped adaptor, such that ligating steps, PCR amplification cycles, overall time-consuming and cost-consuming are reduced on the CG sequencing platform, thereby improving efficiency thereof.

The present disclosure achieves the above objects by the following technical solution.

In a first aspect, the present disclosure provides in embodiments a method of constructing a sequencing library, including:

1) fragmenting a double stranded DNA sample, and subjecting a double stranded DNA fragment obtained to end-repairing, phosphorylation at the 5'-terminal and adenine (A) addition to the 3'-terminal;

2) ligating an adaptor element 1 to both ends of the DNA fragment obtained in step 1), in which
the adaptor element 1 includes a long-chain nucleic acid and a short-chain nucleic acid, which are capable of being annealed to form a first hybrid in a bubble shape with paired regions at two terminals and a non-paired region in the middle,
the first hybrid has a phosphorylated base at the 5'-terminal of the long-chain nucleic acid A and an overhung Thymine (T) at the 3'-terminal of the short-chain nucleic acid B,
the adaptor element 1 contains a recognition site of class III restriction endonuclease;

3) subjecting the DNA fragment obtained in step 2) as a template to PCR amplification with a first pair of primers, which are two single stranded nucleic acids targeting partial sequences of the long-chain nucleic acid and the short-chain nucleic acid of the adaptor element 1 respectively, in which
the first pair of primers each contains a site in the middle thereof, preferably Uracil (U) or deoxyuridine (dU), recognizable and digestible by an enzyme, preferably a USER enzyme;

4) cyclizing the amplified fragment obtained in step 3) with two sticky ends thereof generated by enzyme-digestion, to obtain a cyclic double stranded nucleic acid;

5) digesting the cyclic double stranded nucleic acid obtained in step 4) with the class III restriction endonuclease followed by collection;

6) subjecting the digested DNA fragment obtained in step 5) to end-repairing and adenine (A) addition to the 3'-terminal;

7) ligating an adaptor element 2 to both ends of the DNA fragment obtained in step 6), in which
the adaptor element 2 includes a long-chain nucleic acid and a short-chain nucleic acid, which are capable of being annealed to form a second hybrid in a bubble shape with paired regions at two terminals and a non-paired region in the middle,
the second hybrid has a phosphorylated base at the 5'-terminal of the long-chain nucleic acid A' and an overhung Thymine (T) at the 3'-terminal of the short-chain nucleic acid B',
the adaptor element 2 has a sequence different from that of the adaptor element 1;

8) subjecting the DNA fragment obtained in step 7) as a template to PCR amplification with a second pair of primers, which are two single stranded nucleic acids targeting partial sequences of the long-chain nucleic acid and the short-chain nucleic acid of the adaptor element 2 respectively, in which
one of the two primers is phosphorylated at the first base from the 5'-terminal thereof, and the other one of the two primers is labeled with a biotin at the first base from the 5'-terminal thereof;

9) capturing the PCR product obtained in step 8) with avidin-coated magnetic beads followed by denaturation, and isolating and collecting a non-biotin-labeled single stranded nucleic acid,
preferably, the avidin-coated magnetic beads are streptavidin-coated magnetic beads;
preferably, the PCR product obtained in step 8) is denatured in an alkaline solution or under a high temperature; and 10) cyclizing the non-biotin-labeled single stranded nucleic acid obtained in step 9) to form a cyclic single stranded nucleic acid, i.e., a sequencing library;
preferably, the non-biotin-labeled single stranded nucleic acid is cyclized with a bridge fragment having two ends capable of complementary combining with two terminals of the non-biotin-labeled single stranded nucleic acid;
preferably, the method further includes: digesting the non-biotin-labeled single stranded nucleic acid which is not cyclized after cyclization in step 10), more preferably with at least one of exonuclease 1 and exonuclease 3.

For the above method, as preferred, the double stranded DNA fragment in step 1) is prepared by the following steps:

1a) fragmenting an mRNA sample so as to obtain fragmented mRNA; and 1b) subjecting the fragmented mRNA to reverse transcription, so as to obtain a cDNA amplification product as a double stranded DNA fragment;

optionally, the double stranded DNA fragment is obtained by fragmentation directly from a DNA sample;

preferably, the double stranded DNA sample is fragmented in such a physical or chemical way, more preferably physical ultrasound or enzyme digestion, that the double stranded DNA sample is randomly broken or cleaved;

preferably, the double stranded DNA fragment is end-repaired with T4 DNA polymerase;

preferably, the double stranded DNA fragment after end-repaired is phosphorylated with a nucleotide kinase, preferably T4 polynucleotide kinase;

preferably, the double stranded DNA fragment after end-repaired and phosphorylated is added with adenine (A) at the 3'-terminal using Klenow polymerase without 3' to 5'exonuclease activity.

As preferred, the recognition site of class III restriction endonuclease in the adaptor element 1 is recognizable by Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I or Taq II;

preferably, the recognition site of class III restriction endonuclease is 0-2 bp away from where the adaptor element is ligated to the DNA fragment;

preferably, the long-chain nucleic acid of the adaptor element 1 includes a barcode sequence; further preferably, the barcode sequence has a length of 6 nt to 10 nt.

In a preferred embodiment, the long-chain nucleic acid of the adaptor element 1 has a sequence of 5'-/Phos/ACTGCTGAGTCGAGA(N)CTGACAAGGTCGCCAGCCCTGA

GTGCTTCGAA-3', in which /Phos/ represents a phosphorylation modification, N is a barcode sequence, preferably, the barcode sequence has a length of 6 nt to 10 nt, more preferably, the barcode sequence is 5'-TGTCATAAAT-3'; that is, in a more preferred particular embodiment, the long-chain nucleic acid of the adaptor element 1 has a sequence of (SEQ ID NO: 1)
5'-/Phos/ACTGCTGAGTCGAGATGTCATAAATCTGACAAGGTCGCCA

GCCCTGAGTGCTTCGAA-3';

the short-chain nucleic acid of the adaptor element 1 has a sequence of (SEQ ID NO: 2)
5'-CGAAGCACTCAAGGTCGCCAGCCCTCAGTACGTCAGCAGTT-3'.

When the adaptor element 1 described above is used, it is preferable that the first pair of primers used for PCR amplification in step 3) includes:

a forward primer having a sequence of 5'-AGGUCGC-CAGCCCUCAGTAC-3' (SEQ ID NO:5), and a reverse primer having a sequence of 5'-AGGGCUG-GCGACCUTGTCAG-3' (SEQ ID NO:6).

When the adaptor element 1 described above is used, it is preferable that the long-chain nucleic acid of the adaptor element 2 has a sequence of (SEQ ID NO: 3)
5'-/Phos/AGTCGGAGGCCAAGCGTGCTTAGGATGAGTGCTCTCGA

A-3', in which /Phos/ represents a phosphorylation modification; and the short-chain nucleic acid of the adaptor element 2 has a sequence of 5'-CGAGAGCACTCCATGTAGTGTAC-GATCCGACTT-3' (SEQ ID NO:4).

When the adaptor element 2 described above is used, it is preferable that the second pair of primers used for PCR amplification in step 8) includes:

a forward primer having a sequence of 5'-TC-CTAAGCACGCTTGGCCT-3' (SEQ ID NO:7), and a reverse primer having a sequence of 5'-CATGTAGTG-TACGATCCGACTT-3' (SEQ ID NO:8), in which the forward primer is labeled with a biotin at the first base from the 5'-terminal thereof, and the reverse primer is phosphorylated at the first base from the 5'-terminal thereof.

When the adaptor element 2 described above is used, it is preferable that the bridge fragment in step 10) has a sequence of 5'-GTACACTACATGTCCTAAGCACGC-3' (SEQ ID NO:9).

In a second aspect, the present disclosure provides in embodiments a library obtained by the method as described in the first aspect.

In a third aspect, the present disclosure provides in embodiments the use of the sequencing library as described in the second aspect in sequencing a genome, preferably targeted sequencing;

preferably, the sequencing library is sequenced on a platform that is used for sequencing a cyclic single stranded nucleic acid library, preferable the CG sequencing platform.

In a fourth aspect, the present disclosure provides in embodiments a method of sequencing nucleic acid, including sequencing the library as described in the second aspect, preferably on a platform that is used for sequencing a cyclic single stranded nucleic acid library, more preferably on the CG sequencing platform, preferably, the method further includes at least one of assembling and connecting the sequencing results.

Beneficial Effects

Figure 1:
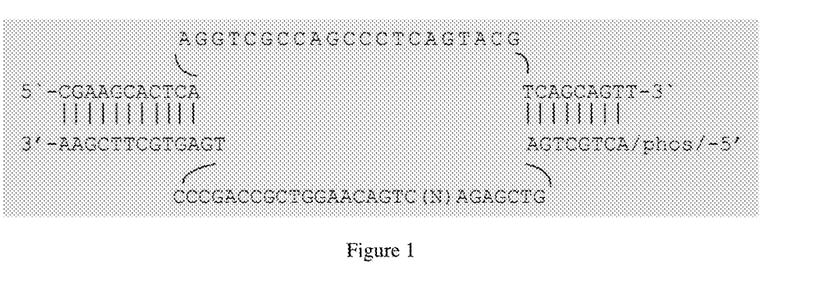
FIG. 1 shows a structure of the first hybrid formed by annealing of the adaptor element 1 in an embodiment of the present disclosure.
Figure 2:
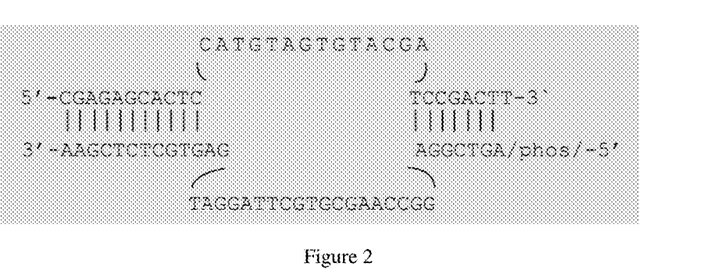
FIG. 2 shows a structure of the second hybrid formed by annealing of the adaptor element 2 in an embodiment of the present disclosure.
Figure 3:
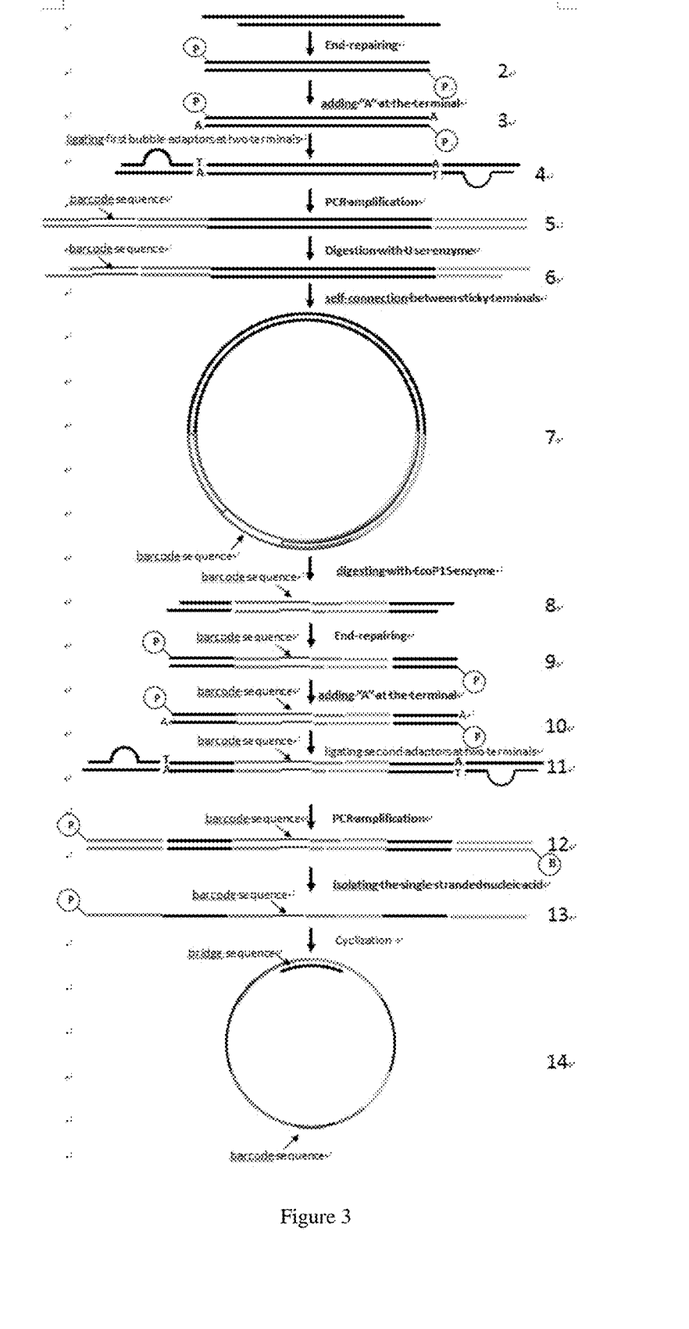
FIG. 3 illustrates a scheme of constructing a sequencing library in an embodiment of the disclosure; in which ⓟ represents phosphorylation to a base; ⓑ represents a biotin is labeled to a base.

In the related art, a sequencing library is constructed by ligating four different adaptors (with different sequence structures) in two ligating steps, i.e., two different adaptors are ligated at two terminals in each ligating step. Such an adaptor-ligated product after each ligating step requires several follow-up processes for subsequent PCR amplification. In contrast, according to embodiments of the present disclosure, the adaptor in the bubble shape is ligated to the DNA fragment respectively at the 3'-terminal and the 5'-terminal (i.e., two bubble-shaped adaptors with same sequences are ligated in one step), resulting in an adaptor-ligated product suitable for direct PCR amplification. Accordingly, the library construction is achieved only with two bubble-shaped adaptors with same sequences (as shown in FIGS. 1 and 2). In specific, the PCR amplification is achieved with a primer complementary to the 3'-terminal of the long-chain nucleic acid of the bubble-shaped adaptor, so as to replace the non-paired sequence in the short-chain nucleic acid, such that the adaptor-ligated product can be amplified directly without intermediate processes and the DNA fragment can be ligated with two different sequences respectively at two terminals, thereby reducing time and material cost for library construction. Accordingly, library construction is optimized by the method provided in embodiments of the present disclosure, such that the ligating steps, time-consuming and cost-consuming of the library construction are reduced, thereby improving efficiency thereof.

BRIEF DESCRIPTION OF THE DRAWINGS

1 is a broken DNA fragment.

2 is a fragment after end-repairing and phosphorylation.

3 is a DNA fragment containing adenine at the 3' terminal.

4 is a DNA fragment after ligated with the adaptor elements 1 respectively at two terminals.

5 is a DNA fragment obtained by PCR amplification of the DNA fragment ligated with two adaptor elements 1.

6 is a DNA fragment having sticky ends after digested by USER enzyme.

7 is cyclic double stranded nucleic acid formed by cyclization with sticky ends.

8 is a linear DNA fragment formed by digestion with class III restriction endonucleases.

9 is a DNA fragment after end-repairing and phosphorylation.

10 is a DNA fragment containing adenine (A) at the 3' terminal.

11 is a DNA fragment after ligated with the adaptor elements 2 respectively at two terminals.

12 is a DNA fragment obtained by PCR amplification of the DNA fragment ligated with two adaptor elements 2.

13 is a single stranded DNA fragment isolated by avidin-coated magnetic beads.

14 is the final product of library construction, i.e. a cyclic single stranded DNA.

DETAILED DESCRIPTION

For the purpose of understanding the present disclosure, the present disclosure is exemplified as follows. It will be apparent to those skilled in the art that the examples are merely illustrative and should not be construed as a particular limit of the disclosure.

Example 1 the Process of Constructing a Sequencing Library Proposed by the Present Disclosure 1. Fragmenting a Genome 1 µg genomic DNA sample extracted from human lymphoid tissue (Yanhuang), after diluted with TE buffer up to 80 µl in a plate dedicated to fragmentation on Covaris, was fragmented on a Covaris LE220 sonicator, thereby obtaining DNA fragments each having a length of 200 bp to 400 bp. The parameters for fragmentation are shown in the following table:

| Filling factor | 21% |
| Pressure (PIP) | 500 |
| Pulse factor | 500 |
| Fragmentation period | 20 s, 6 times |

The fragmented genome sample was mixed with 64 µl Ampure XP magnetic beads to be uniform in a new 1.5 ml non-stick EP tube, followed by still standing at room temperature for 5 minutes and then placed onto a magnetic separator for 5 minutes. Resulting supernatant was collected and mixed with additional 32 µl Ampure XP magnetic beads to be uniform in another new non-stick EP tube, followed by still standing at room temperature for 5 minutes and placed onto the magnetic separator for 5 minutes. After discarding supernatant thus obtained, the remaining magnetic beads were washed twice with 75% ethanol. Those dried magnetic beads were then dissolved in 42 µl TE buffer or enzyme-free water to retrieve fragmented DNA, followed by still standing for 5 minutes.

2. End-Repairing to Fragmented DNA

A first premixed solution for end-repairing reaction was formulated in advance with the components listed in the table below.

| 10× Polynucleotide kinase buffer | 5.5 µl |
| 25 mM Deoxynucleotides triphosphates | 3 µl |
| T4 DNA Polymerases | 3 µl |
| T4 Polynucleotide kinases | 3 µl |
| Klenow Fragments | 1 µl |
| Total volume | 15.5 µl |

The fragmented DNA obtained in step 1 was mixed with the first premix solution to be uniform, followed by incubation at 20° C. for 30 minutes. Subsequently, the resulting product was mixed with 60 µl Ampure XP magnetic beads to be uniform, followed by still standing for 5 minutes. After discarding supernatant thus obtained, the remaining magnetic beads were washed twice with 75% ethanol. Those dried magnetic beads were then dissolved in 42 µl TE buffer to retrieve end-repaired DNA fragments (Such a process is a standard procedural for DNA purification with magnetic beads, which was also used hereinafter without detailed elaboration for concise, unless otherwise specified).

3. Adding "A" to the End-Repaired DNA Fragment Respectively at Two Terminals

A second premixed solution was formulated in advance with the components listed in the table below.

| 10× Blue Buffer (Enzymatics) | 5 µl |
| 10 mM ATP | 1 µl |

-continued

| | |
|---|---|
| Klenow (3' to 5' exo-) Enzyme | 2 μl |
| Enzyme-free water | 2 μl |
| Total volume | 10 μl |

The end-repaired DNA fragments obtained in step 2 were mixed with the second premixed solution to be uniform, followed by incubation at 37° C. for 30 minutes. Subsequently, the resulting product was mixed with 50 μl Ampure XP magnetic beads for purification. Those dried magnetic beads were then dissolved in 42 μl TE buffer to retrieve end-repaired DNA fragments with "A" at the terminals.

4. Ligating the Adaptor Element 1

The adaptor element 1 is of a sequence structure as shown in FIG. 1, in which a barcode sequence N having a sequence of 5'-TGTCATAAAT-3' is included.

A third pre-mixed solution was formulated in advance with the components listed in the table below.

| | |
|---|---|
| 10× Ligation Buffer (Enzymatics) | 5 μl |
| Adaptor element 1 (20 μM) | 2 μl |
| Total volume | 7 μl |

The end-repaired DNA fragments with "A" at the terminals obtained in step 3 were mixed with the third pre-mixed solution to be uniform, followed by addition of 2 μl T4 DNA ligase and then incubation at 20° C. for 1 hour. After purification with Ampure XP magnetic beads, the DNA fragment ligated with the adaptor element 1 was dissolved in 42 μl TE buffer.

5. First PCR Amplification

The primer 1 has a sequence of 5'-AGGUCGCCAGCC-CUCAGTAC-3'; and the primer 2 has a sequence of 5'-AGGGCμGGCGACCUTGTCAG-3'.

A fourth premixed solution was formulated in advance with the components listed in the table below.

| | |
|---|---|
| Enzyme-free water | 4 μl |
| 10× PfuTurbo Cx Buffer (Agilent) | 50 μl |
| PfuTurbo Cx Hot start nucleic acid polymerase (2.5 U/μl) (Agilent) | 2 μl |
| 20 μM Primer 1 | 2 μl |
| 20 μM Primer 2 | 2 μl |
| Total volume | 60 μl |

The DNA fragment ligated with the adaptor element 1 obtained in step 4 was mixed with the fourth premixed solution to be uniform, followed by first PCR amplification with the procedures as shown in the table below.

| | | |
|---|---|---|
| 95° C. | 3 min | |
| 95° C. | 30 s | |
| 56° C. | 30 s | 7 cycles |
| 72° C. | 90 s | |
| 68° C. | 7 min | |

After the first PCR amplification, the amplified DNA was purified with 100 μl Ampure XP magnetic beads, and then dissolved in 82 μl TE buffer.

6. Enzyme-Digesting at Uracil

A fifth premixed solution was formulated in advance with the components listed in the table below.

| | |
|---|---|
| Enzyme-free water | 5.8 μl |
| 10× Taq Buffer (Takara) | 11 μl |
| USER Enzyme (1000 U/ml) | 13.2 μl |
| Total volume | 30 μl |

The amplified DNA obtained in step 5 was mixed with the fifth premixed solution to be uniform, followed by incubation at 37° C. for 1 h.

7. Cyclizing the Double Stranded DNA with Sticky Terminals

A reaction system 1 was formulated with the components listed below.

| | |
|---|---|
| Enzyme-free water | 1520 μl |
| 10× TA Buffer (epicenter) | 180 μl |
| Total volume | 1700 μl |

The double stranded DNA with sticky terminals obtained in step 6 was mixed with the reaction system 1 to be uniform followed by incubation at 60° C. for 30 min, after which a first product thus obtained was kept at 24° C.

A reaction system 2 was formulated with the components listed below.

| | |
|---|---|
| Enzyme-free water | 194 μl |
| T4 DNA Ligase (Rapid)(600 U/μl)(enzymatics Company) | 6 μl |
| Total volume | 200 μl |

The first product was mixed with the reaction system 2 to be uniform, followed by incubation at 24° C. for 1 h, thereby obtaining a second product.

The second product was mixed with 1320 μl Ampure XP magnetic beads to be uniform, followed by still standing for 5 minutes and then placed onto a magnetic separator for adsorption. Resulting supernatant was collected and mixed with additional 680 μl Ampure XP magnetic beads to be uniform, followed by still standing for 5 minutes and placed onto the magnetic separator for adsorption. After discarding supernatant thus obtained, the remaining magnetic beads were washed twice with 75% ethanol. Those dried magnetic beads were then dissolved in 65 μl TE buffer or enzyme-free water to retrieve a DNA product after cyclization, followed by still standing for 5 minutes.

8. Removing Non-Cyclic Double Stranded DNA

A sixth premixed solution was formulated in advance with the components listed in the table below.

| | |
|---|---|
| Enzyme-free water | 2 μl |
| Plasmid-protected 10× Reaction buffer (Epicentre) | 8 μl |
| Plasmid-protected adenosine triphosphate dependent DNA nuclease (Epicentre) | 10 μl |
| Total volume | 20 μl |

The DNA product after cyclization obtained in step 7 was mixed with the sixth premixed solution to be uniform, followed by incubation at 37° C. for 1 h, so as to digest and remove linear DNA which was not cyclized after cyclization. The cyclic double stranded DNA thus collected was purified with 80 μl Ampure XP magnetic beads, and dissolved in 42 μl TE buffer or enzyme-free water.

9. Digesting the Cyclic Double Stranded DNA with Ecop15

A seventh premixed solution was formulated in advance with the components listed in the table below.

| Enzyme-free water | 274 μl |
|---|---|
| 10× NEBuffer3.1(NEB) | 36 μl |
| Ecop15 I Endonuclease (10 U/μl) | 10 μl |
| Total volume | 320 μl |

The cyclic double stranded DNA obtained in step 8 was mixed with the seventh premixed solution to be uniform, followed by incubation at 37° C. for 16 h.

After reaction, the resulting double stranded DNA after digestion was mixed with 415 μl Ampure XP magnetic beads to be uniform, followed by still standing for 5 minutes and then placed onto a magnetic separator for adsorption. Resulting supernatant was collected and mixed with additional 296 μl Ampure XP magnetic beads to be uniform, followed by still standing for 5 minutes and placed onto the magnetic separator for adsorption. After discarding supernatant thus obtained, the remaining magnetic beads were washed twice with 75% ethanol. Those dried magnetic beads were then dissolved in 42 μl TE buffer or enzyme-free water to retrieve a DNA product after digestion, followed by still standing for 5 minutes.

10. End-Repairing to the Digested Product from the Cyclic Double Stranded DNA

An eighth premixed solution was formulated in advance with the components listed in the table below.

| 10× Polynucleotide kinase buffer | 5.5 μl |
|---|---|
| 25 mM Deoxynucleotides triphosphate | 3 μl |
| T4 DNA Polymerase | 3 μl |
| T4 Polynucleotide kinase | 3 μl |
| Klenow Fragment | 1 μl |
| Total volume | 15.5 μl |

The digested product from the cyclic double stranded DNA obtained in step 9 was mixed with the eighth premixed solution to be uniform, followed by incubation at 20° C. for 30 minutes. The end-repaired product thus obtained was purified with 60 μl Ampure XP magnetic beads, and dissolved in 42 μl TE buffer for collection.

11. Adding "A" to the end-repaired DNA product respectively at two terminals

A ninth premixed solution was formulated in advance with the components listed in the table below.

| 10× Blue Buffer (Ezymatics) | 5 μl |
|---|---|
| 10 mM ATP | 1 μl |
| Klenow (3'-5' exo-) Enzyme | 2 μl |
| Enzyme-free water | 2 μl |
| Total volume | 10 μl |

The end-repaired DNA product obtained in step 10 was mixed with the ninth premixed solution to be uniform, followed by incubation at 37° C. for 30 minutes. The resulting DNA product with "A" at two terminals thus obtained was purified with 50 μl Ampure XP magnetic beads, and dissolved in 42 μl TE buffer.

12. Ligating the Adaptor Element 2

The adaptor element 2 is of a sequence structure as shown in FIG. 2.

A tenth premixed solution was formulated in advance with the components listed in the table below.

| 10× Ligation Buffer (Enzymatics) | 5 μl |
|---|---|
| Adaptor element 2 (20 μM) | 2 μl |
| Total volume | 7 μl |

The DNA product added with "A" at two terminals obtained in step 11 was mixed with the tenth premixed solution to be uniform, followed by addition of 2 μl T4 DNA ligase and then incubation at 20° C. for 1 hour. After purification with Ampure XP magnetic beads, the DNA product ligated with the adaptor element 2 was dissolved in 42 μl TE buffer.

13. Second PCR Amplification

The primer 3 has a sequence of 5'-TCCTAAGCACGCT-TGGCCT-3', in which the first base T from the 5' terminal is labeled with a biotin, and the primer 4 has a sequence of 5'-CATGTAGTGTAC-GATCCGACTT-3', in which the first base C from the 5' terminal is phosphorylated.

An eleventh premixed solution was formulated in advance with the components listed in the table below.

| Enzyme-free water | 4 μl |
|---|---|
| 10× PfuTurbo Cx Buffer (Agilent) | 50 μl |
| PfuTurbo Cx Hot start nucleic acid polymerase (2.5 U/μl) (Agilent) | 2 μl |
| 20 μM Primer 3 | 2 μl |
| 20 μM Primer 4 | 2 μl |
| Total volume | 60 μl |

The DNA product ligated with the adaptor element 2 obtained in step 12 was mixed with the eleventh premixed solution to be uniform, followed by second PCR amplification with the procedures as shown in the table below.

| 95° C. | | 3 min | |
|---|---|---|---|
| 95° C. | 30 s | | |
| 56° C. | 30 s | | 7 cycles |
| 72° C. | 90 s | | |
| 68° C. | | 7 min | |

After the second PCR amplification, the amplified DNA product was purified with 100 μl Ampure XP magnetic beads, and then dissolved in 62 μl TE buffer.

14. Isolating and Cyclizing Single Stranded DNA

Streptavidin-coated beads (Dynabeads® MyOne™ Streptavidin, Life technologies) were equilibrated at room temperature for half an hour in advance. 30 μl of the equilibrated beads was mixed with 120 μl of 1×magnetic bead binding buffer to be uniform in a new centrifuge tube, followed by still standing on the magnetic separator for 5 minutes. After clarified supernatant was removed, the remaining beads were resuspended in additional 30 μl of the 1×magnetic bead binding buffer for later use.

The amplified DNA product after the second PCR amplification obtained in step 13 was diluted and mixed with 20 μl of 4×magnetic bead binding buffer to be uniform. Subsequently, the DNA product diluted in the 4×magnetic bead binding buffer was mixed with the re-suspended magnetic beads to be uniform, followed by incubation at room temperature for 5 minutes allowing hybridization and then still standing on the magnetic separator for 5 minutes allowing adsorption. After discarding supernatant thus obtained, the remaining magnetic beads were re-suspended with 1 ml of 1×bead washing buffer and still standing on the magnetic separator for 5 minutes allowing adsorption. After the resulting supernatant was discarded, the above process was repeated once. The remaining magnetic beads thus obtained were mixed with 78 µl of 0.1M sodium hydroxide solution, followed by still standing for 5 minutes and then placed onto the magnetic separator for 5 minutes. The resulting supernatant was collected and then mixed with 37.5 µl MOPS buffer to be uniform in a new centrifuge tube, thereby isolating the single stranded DNA.

A cyclization premixed solution 1 was formulated in advance with the components listed in the table below, in which the bridge sequence has a sequence as shown in SEQ ID NO: 9, i.e. 5'-GTACACTACATGTCCTAAGCACGC-3'):

| | |
|---|---|
| Enzyme-free water | 43 µl |
| Bridge sequence | 20 µl |
| Total | 63 µl |

A cyclization premixed solution 2 was formulated in advance with the components listed in the table below.

| | |
|---|---|
| Enzyme-free water | 135.3 µl |
| 10× TA Buffer (epicenter) | 35 µl |
| 100 mM Adenosine triphosphate | 3.5 µl |
| T4 DNA Ligase (Rapid)(600 U/µl)(enzymatics Company) | 1.2 µl |
| In total | 175 µl |

The isolated single stranded DNA was firstly mixed with the cyclization premixed solution 1, and then with the cyclization premixed solution 2, followed by incubation at 37° C. for 1.5 hours.

15. Purification by Removing the Non-Cyclic Single Stranded DNA

A digestion solution was formulated in advance with the components listed in the table below.

| | |
|---|---|
| Enzyme-free water | 1.5 µl |
| 10× TA Buffer (epicenter) | 3.7 µl |
| Exonuclease 1 (20 U/µl) (NEB Company) | 11.1 µl |
| Exonuclease 3 (100 U/µl) (NEB Company) | 3.7 µl |
| In total | 20 µl |

About 350 µl of the resulting product after cyclization in step 14 was mixed with 20 µl of the digestion solution to be uniform, followed by incubation at 37° C. for 30 minutes. After incubation, 15.4 µl of 500 mM ethylenediaminetetraacetic acid was added to reaction system, and mixed to be uniform.

The cyclic single stranded DNA was purified and collected with 800 µl Ampure XP magnetic beads, and dissolved in 40 µl TE buffer, such that the sequencing library containing the cyclic single stranded nucleic acid was obtained, which was further detected by 6% urea denatured PAGE gel. The results are shown in FIG. 4.

Figure 4:
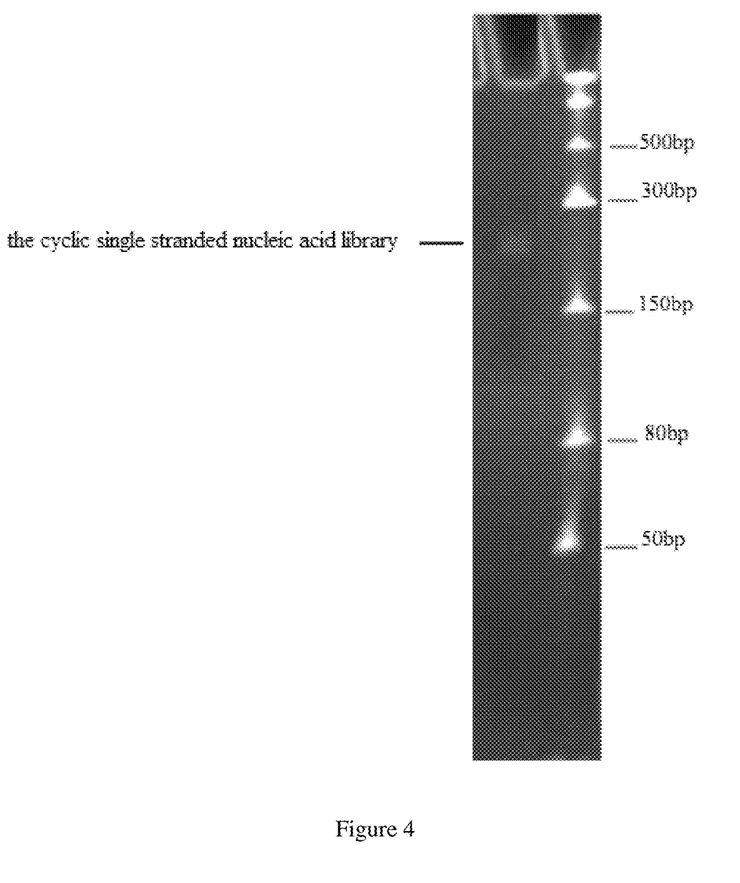
FIG. 4 is an electrophoresis result showing the sequencing library constructed according to embodiments of the present disclosure, in which the left lane: is a cyclic single stranded DNA library; and the right lane: Low Range RNA Ladder (FERMENTAS).

The electrophoresis result in FIG. 4 shows that the cyclic single stranded DNA is concentrated which indicates that the sequencing library constructed is in good quality. It has been proved in the above example that the technical solution proposed in the present disclosure is completely feasible.

The Applicant has stated that the present disclosure illustrates the detailed process equipment and process flow of the present disclosure by the examples described above, but the present disclosure is not limited to the detailed process equipment and process flow described above, that is it is not meant that the present disclosure has to rely on the detailed process equipment and process described above to be implemented. It will be apparent to those skilled in the art that any improvements to the present disclosure, equivalents of the raw materials of the present disclosure and addition of auxiliary ingredients, selection of specific means and the like all fall within the scope of the protection and disclosure of the present disclosure.

What is claimed is:

1. A method of constructing a sequencing library, comprising:
   1) fragmenting a double stranded DNA sample, and subjecting a double stranded DNA fragment obtained to end-repairing, phosphorylation at the 5'-terminal and adenine (A) addition to the 3'-terminal;
   2) ligating an adaptor element 1 to both ends of the DNA fragment obtained in step 1), wherein
      the adaptor element 1 comprises a long-chain nucleic acid and a short-chain nucleic acid, which are capable of being annealed to form a first hybrid in a bubble shape with paired regions at two terminals and a non-paired region in the middle,
      the first hybrid has a phosphorylated base at the 5'-terminal of the long-chain nucleic acid A and an overhung Thymine (T) at the 3'-terminal of the short-chain nucleic acid B, and
      the adaptor element 1 contains a recognition site of class III restriction endonuclease;
   3) subjecting the DNA fragment obtained in step 2) as a template to PCR amplification with a first pair of primers, which are two single stranded nucleic acids targeting partial sequences of the long-chain nucleic acid and the short-chain nucleic acid of the adaptor element 1 respectively, wherein
      the first pair of primers each contains a site in the middle thereof recognizable and digestible by an enzyme;
   4) cyclizing the amplified fragment obtained in step 3) with two sticky ends thereof generated by enzyme-digestion, to obtain a cyclic double stranded nucleic acid;
   5) digesting the cyclic double stranded nucleic acid obtained in step 4) with the class III restriction endonuclease followed by collection;
   6) subjecting the digested DNA fragment obtained in step 5) to end-repairing and adenine (A) addition to the 3'-terminal;
   7) ligating an adaptor element 2 to both ends of the DNA fragment obtained in step 6), wherein
      the adaptor element 2 comprises a long-chain nucleic acid and a short-chain nucleic acid, which are capable of being annealed to form a second hybrid in a bubble shape with paired regions at two terminals and a non-paired region in the middle,
      the second hybrid has a phosphorylated base at the 5'-terminal of the long-chain nucleic acid A' and an overhung Thymine (T) at the 3'-terminal of the short-chain nucleic acid B', and
      the adaptor element 2 has a sequence different from that of the adaptor element 1;
   8) subjecting the DNA fragment obtained in step 7) as a template to PCR amplification with a second pair of primers, which are two single stranded nucleic acids targeting partial sequences of the long-chain nucleic acid and the short-chain nucleic acid of the adaptor element 2 respectively, wherein
      one of the two primers is phosphorylated at the first base from the 5'-terminal thereof, and the other one of the two primers is labeled with a biotin at the first base from the 5'-terminal thereof;
   9) capturing the PCR product obtained in step 8) with avidin-coated magnetic beads followed by denaturation, and isolating and collecting a non-biotin-labeled single stranded nucleic acid; and
   10) cyclizing the non-biotin-labeled single stranded nucleic acid obtained in step 9) to form a cyclic single stranded nucleic acid, i.e., a sequencing library.

2. The method according to claim 1, wherein the double stranded DNA fragment in step 1) is prepared by the following steps:
   1a) fragmenting an mRNA sample so as to obtain fragmented mRNA; and
   1b) subjecting the fragmented mRNA to reverse transcription, so as to obtain a cDNA amplification product as a double stranded DNA fragment.

3. The method according to claim 1, wherein the recognition site of class III restriction endonuclease in the adaptor element 1 is recognizable by Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I or Taq II.

4. The method according to claim 1, wherein the long-chain nucleic acid of the adaptor element 1 has a sequence of 5'-/Phos/ACTGCTGAGTCGAGA(N)CTGACAAGGTCGCCAGCCCTGA GTGCTTCGAA-3', wherein /Phos/ represents a phosphorylation modification, N is a barcode sequence; and
   the short-chain nucleic acid of the adaptor element 1 has a sequence of

5'-CGAAGCACTCA AGGTCGCCAGCCCTCAGTACGTCAGCAGTT-3'.

5. The method according to claim 4, wherein the first pair of primers used for PCR amplification in step 3) comprises:
   a forward primer having a sequence of 5'-AGGUCGC-CAGCCCUCAGTAC-3', and
   a reverse primer having a sequence of 5'-AGGGCUG-GCGACCUTGTCAG-3'.

6. The method according to claim 1, wherein the long-chain nucleic acid of the adaptor element 2 has a sequence of

```
5'-/Phos/AGTCGGAGGCCAAGCGTGCTTAGGATGAGTGCTCTCGA
A-3',
``` wherein /Phos/ represents a phosphorylation modification; and the short-chain nucleic acid of the adaptor element 2 has a sequence of 5'-CGAGAGCACTCCATGTAGTGTACGATCCGACTT-3'.

7. The method according to claim 6, wherein the second pair of primers used for PCR amplification in step 8) comprises:

a forward primer having a sequence of 5'-TCCTAAGCACGCTTGGCCT-3', and a reverse primer having a sequence of 5'-CATGTAGTGTACGATCCGACTT-3', wherein the forward primer is labeled with a biotin at the first base from the 5'-terminal thereof, and the reverse primer is phosphorylated at the first base from the 5'-terminal thereof.

8. The method according to claim 1, wherein the PCR product obtained in step 8) is denatured in an alkaline solution or under a high temperature.

9. The method according to claim 1, wherein the non-biotin-labeled single stranded nucleic acid is cyclized with a bridge fragment having two ends capable of complementary combining with two terminals of the non-biotin-labeled single stranded nucleic acid.

10. The method according to claim 1, wherein the method further comprises: digesting the non-biotin-labeled single stranded nucleic acid which is not cyclized after cyclization in step 10) with at least one of exonuclease 1 and exonuclease 3.

11. The method according to claim 1, wherein the double stranded DNA fragment is obtained by fragmentation directly from a DNA sample.

12. The method according to claim 1, wherein the double stranded DNA sample is fragmented in such a physical or chemical way that the double stranded DNA sample is randomly broken or cleaved.

13. The method according to claim 1, wherein the double stranded DNA fragment is end-repaired with T4 DNA polymerase.

14. The method according to claim 1, wherein the double stranded DNA fragment after end-repaired is phosphorylated with a T4 polynucleotide kinase.

15. The method according to claim 1, wherein the double stranded DNA fragment after end-repaired and phosphorylated is added with adenine (A) at the 3'-terminal using Klenow polymerase without 3' to 5'exonuclease activity.

16. The method according to claim 1, wherein the recognition site of class III restriction endonuclease is 0-2 bp away from where the adaptor element is ligated to the DNA fragment.

17. The method according to claim 1, wherein the long-chain nucleic acid of the adaptor element 1 comprises a barcode sequence having a length of 6 nt to 10 nt.

18. The method according to claim 17, wherein the barcode sequence is 5'-TGTCATAAAT-3'.

19. The method according to claim 1, wherein the bridge fragment in step 10) has a sequence of 5'-GTACACTACATGTCCTAAGCACGC-3'.

20. The method according to claim 1, wherein the first pair of primers each contains Uracil (U) or deoxyuridine (dU) in the middle thereof recognizable and digestible by a USER enzyme.

* * * * *

UNITED STATES PATENT AND TRADEMARK OFFICE
CERTIFICATE OF CORRECTION

PATENT NO.        : 10,316,356 B1
APPLICATION NO.   : 15/528353
DATED             : June 11, 2019
INVENTOR(S)       : Yuan Jiang et al.

Page 1 of 1

It is certified that error appears in the above-identified patent and that said Letters Patent is hereby corrected as shown below:

On the Title Page

Under item (87), PCT Pub. Date:
Delete "May 26, 2015" and insert -- May 26, 2016 --

Signed and Sealed this
Twelfth Day of November, 2019

Andrei Iancu
*Director of the United States Patent and Trademark Office*